US010799315B2

(12) United States Patent
Leung et al.

(10) Patent No.: US 10,799,315 B2
(45) Date of Patent: Oct. 13, 2020

(54) SYSTEMS AND METHODS FOR VERIFICATION OF FIDUCIAL CORRESPONDENCE DURING IMAGE-GUIDED SURGICAL PROCEDURES

(71) Applicant: 7D SURGICAL INC., Toronto (CA)

(72) Inventors: Michael K. K. Leung, Markham (CA); Adrian Mariampillai, Toronto (CA); Beau Anthony Standish, Toronto (CA); Peter Siegler, Toronto (CA); Victor X. D. Yang, North York (CA)

(73) Assignee: 7D SURGICAL INC., Toronto, Ontario (CA)

( * ) Notice: Subject to any disclaimer, the term of this patent is extended or adjusted under 35 U.S.C. 154(b) by 104 days.

(21) Appl. No.: 16/314,923

(22) PCT Filed: Jul. 7, 2017

(86) PCT No.: PCT/CA2017/050830
§ 371 (c)(1),
(2) Date: Jan. 3, 2019

(87) PCT Pub. No.: WO2018/018134
PCT Pub. Date: Feb. 1, 2018

(65) Prior Publication Data
US 2019/0254772 A1 Aug. 22, 2019

Related U.S. Application Data

(60) Provisional application No. 62/366,723, filed on Jul. 26, 2016.

(51) Int. Cl.
*G06K 9/46* (2006.01)
*A61B 90/00* (2016.01)
(Continued)

(52) U.S. Cl.
CPC .............. *A61B 90/37* (2016.02); *A61B 34/00* (2016.02); *A61B 34/20* (2016.02); *G06T 7/0012* (2013.01);
(Continued)

(58) Field of Classification Search
CPC ....................................................... G06K 9/46
See application file for complete search history.

(56) References Cited

U.S. PATENT DOCUMENTS 8,014,575 B2 * 9/2011 Weiss ...................... B60R 25/00
382/128
8,014,625 B2 * 9/2011 Dewaele ............... G06T 3/0068
345/619
(Continued)

FOREIGN PATENT DOCUMENTS

CA        2961079 A1    3/2016
WO     2015074158 A1    5/2015

OTHER PUBLICATIONS

International Search Report for the parent PCT application PCT/CA2017/050770, dated Oct. 31, 2017.
(Continued)

*Primary Examiner* — Cindy Trandai
(74) *Attorney, Agent, or Firm* — Hill & Schumacher

(57) ABSTRACT

Systems and methods are provided for use in image-guided surgical procedures, in which intraoperatively acquired surface data is employed to verify the correspondence between intraoperatively selected fiducial points and volumetric fiducial points, where the volumetric fiducial points are selected based on volumetric image data. Segmented surface data obtained from the volumetric image data is registered to the intraoperative surface data using the intraoperative and volumetric fiducial points for initial surface alignment, and this process is repeated for other permutations of the correspondence between the intraoperatively fiducial points and (Continued)

the volumetric fiducial points. Quality measures may be determined that relate to the registration quality for each fiducial correspondence permutation, where the quality measures may be employed to assess of the likelihood that the initially prescribed fiducial correspondence is correct. A graphical representation may be generated for visually displaying the alignment of the registered surfaces for the different fiducial correspondence permutations.

26 Claims, 12 Drawing Sheets

(51) Int. Cl.
*A61B 34/20* (2016.01)
*G06T 7/11* (2017.01)
*G06T 7/30* (2017.01)
*G06T 7/00* (2017.01)
*A61B 34/00* (2016.01)

(52) U.S. Cl.
CPC ............... *G06T 7/11* (2017.01); *G06T 7/30* (2017.01); *A61B 2034/2065* (2016.02); *A61B 2090/363* (2016.02); *G06T 2207/20101* (2013.01); *G06T 2207/30012* (2013.01)

(56) References Cited

U.S. PATENT DOCUMENTS

| | | | |
|---|---|---|---|
| 8,965,083 B2* | 2/2015 | Ben Ayed | G06T 7/136 382/128 |
| 9,119,670 B2 | 9/2015 | Yang et al. | |
| 9,202,387 B2 | 12/2015 | Gilboa | |
| 10,176,388 B1* | 1/2019 | Ghafarianzadeh | G06K 9/00671 |
| 10,426,556 B2* | 10/2019 | Miga | A61B 8/085 |
| 2008/0063301 A1 | 3/2008 | Bogoni et al. | |
| 2008/0242978 A1* | 10/2008 | Simon | A61B 90/36 600/426 |
| 2010/0014722 A1* | 1/2010 | Rohrer | G06K 9/6207 382/128 |
| 2010/0054525 A1 | 3/2010 | Gong et al. | |
| 2013/0279784 A1 | 10/2013 | Gill et al. | |
| 2015/0173701 A1* | 6/2015 | Major | G06K 9/6297 382/131 |
| 2015/0228070 A1* | 8/2015 | Birkbeck | G06T 7/10 382/131 |
| 2017/0000581 A1* | 1/2017 | Tokuda | G06K 9/6201 |
| 2017/0231713 A1* | 8/2017 | Siewerdsen | A61B 5/4566 382/128 |
| 2017/0337682 A1* | 11/2017 | Liao | G06T 7/30 |
| 2018/0271602 A1* | 9/2018 | Frey | A61B 17/7013 |
| 2018/0301213 A1* | 10/2018 | Zehavi | A61B 6/032 |
| 2019/0021677 A1* | 1/2019 | Grbic | G06K 9/6267 |
| 2019/0035156 A1* | 1/2019 | Wei | G06T 19/006 |
| 2019/0103190 A1* | 4/2019 | Schmidt | G06T 19/20 |

OTHER PUBLICATIONS

Herring, Jeannette and Benoit Dawant, "Automatic Lumbar Vertebral Identification Using Surface-Based Registration", Journal of Biomedical Informatics 34, 74-87, (2001).

* cited by examiner

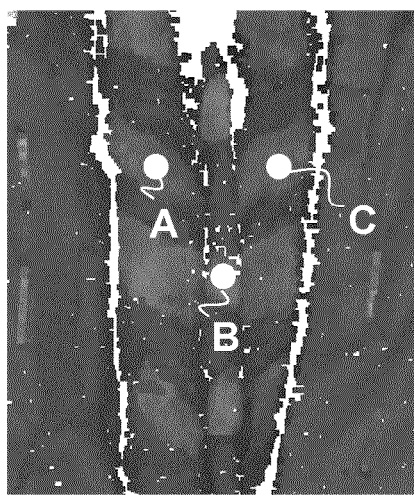
(i)
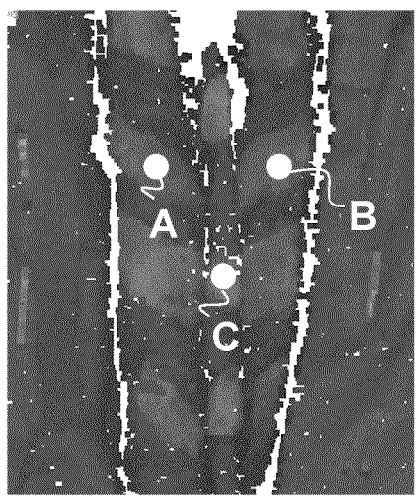
(ii)
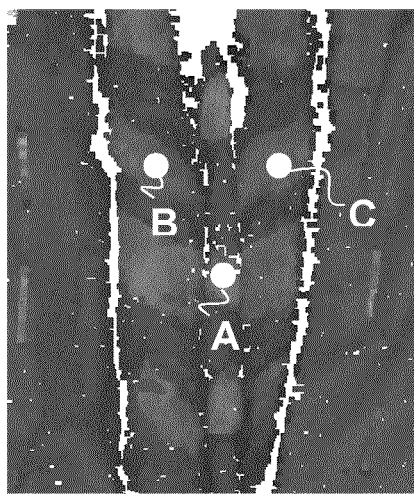
(iii)
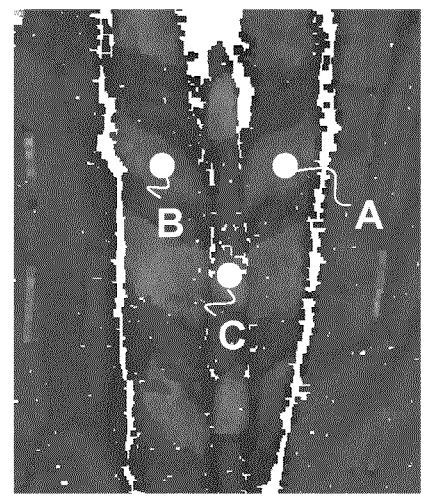
(iv)
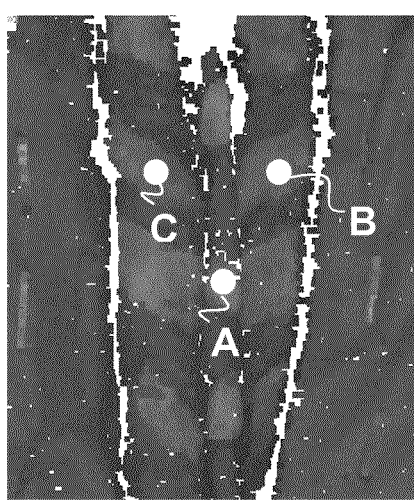
(v)
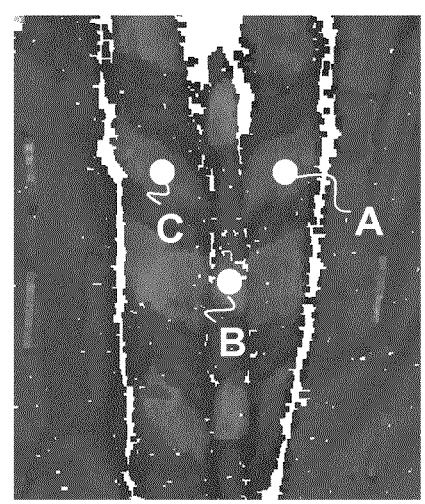
(vi)
FIG. 2E

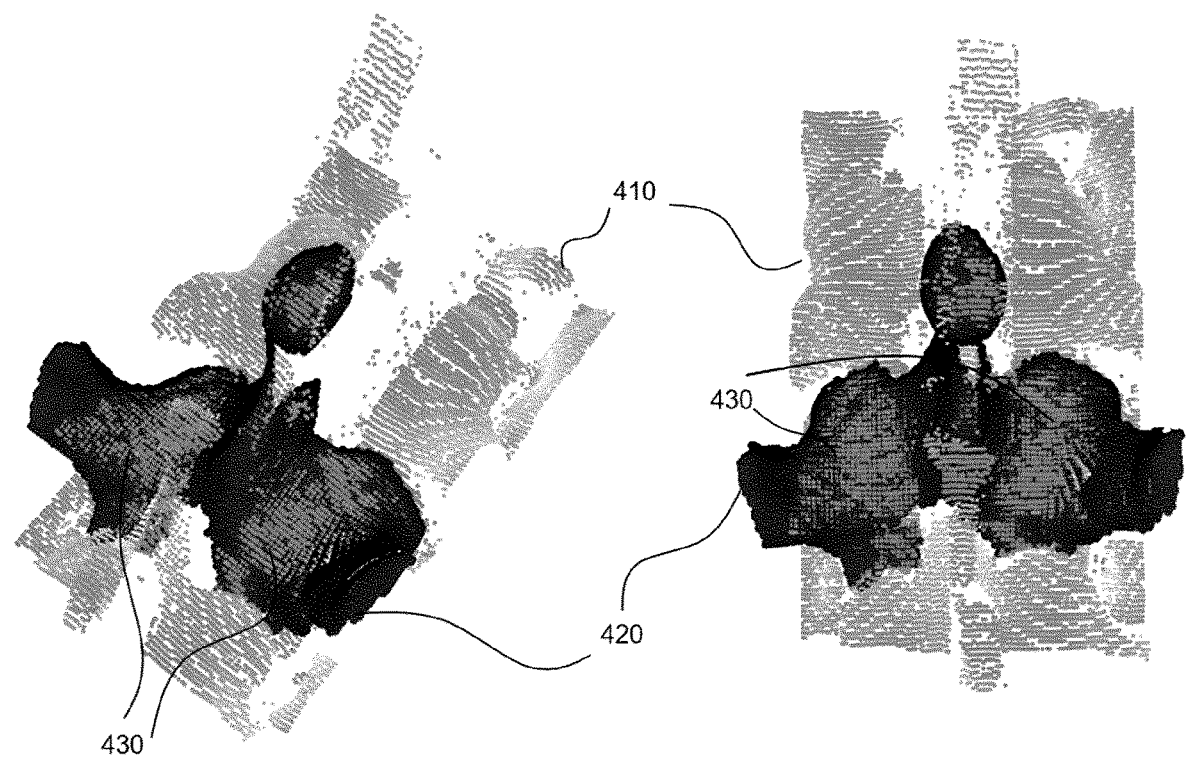
FIG. 3A  FIG. 3B
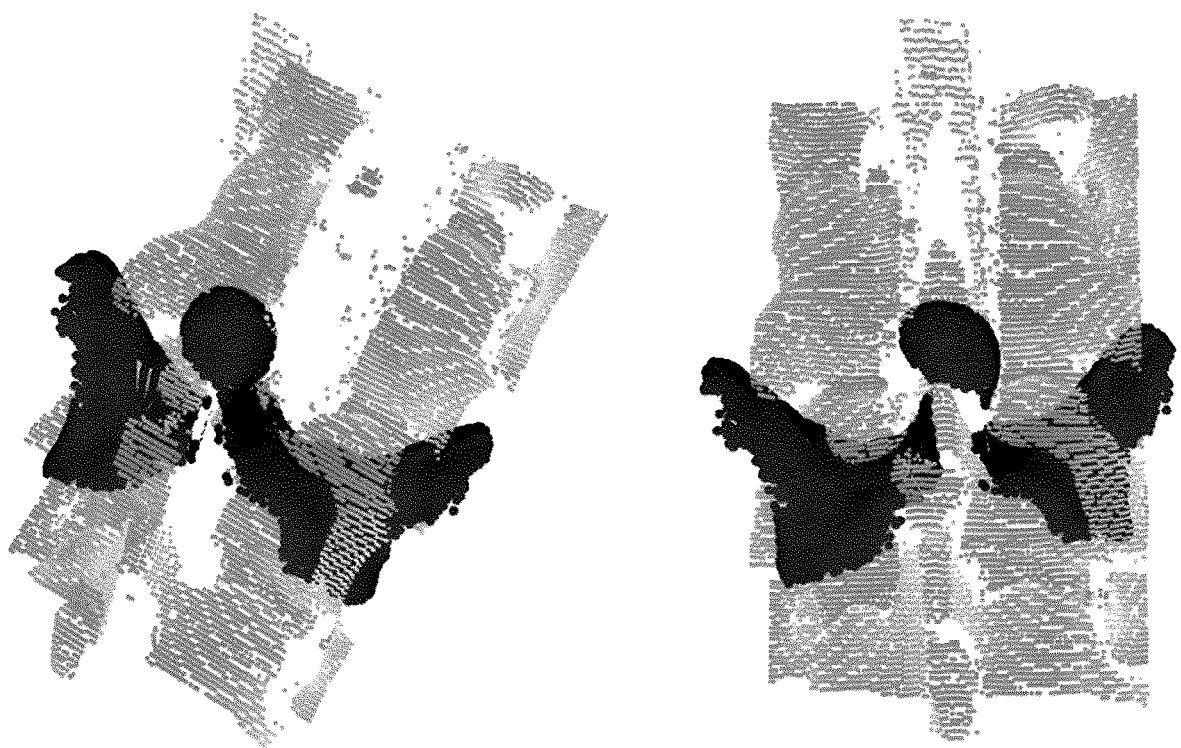
FIG. 3C  FIG. 3D

WARNING!

Please verify that fiducials on the patient match with the fiducials selected on the image.

| Return to Registration | Proceed to Navigation |

FIG. 4A

SYSTEMS AND METHODS FOR VERIFICATION OF FIDUCIAL CORRESPONDENCE DURING IMAGE-GUIDED SURGICAL PROCEDURES

CROSS-REFERENCE TO RELATED APPLICATION

This application is a National Phase application claiming the benefit of the international PCT Patent Application No. PCT/CA2017/050830, filed on Jul. 7, 2017, in English, which claims priority to U.S. Provisional Application No. 62/366,723, titled "SYSTEMS AND METHODS FOR VERIFICATION OF FIDUCIAL CORRESPONDENCE DURING IMAGE-GUIDED SURGICAL PROCEDURES" and filed on Jul. 26, 2016, the entire contents of which are incorporated herein by reference.

BACKGROUND

The present disclosure relates to image-based surgical guidance.

A common problem in the field of image-guided surgery is to correctly associate fiducials in a preoperative volumetric frame of reference with fiducials selected in an intraoperative frame of reference, thereby permitting intraoperative registration of volumetric image data with intraoperatively tracked medical instruments. For example, in surgical procedures involving the spine, fiducials (both volumetric and intraoperative) are usually associated with a spinal level, which means that the surgeon must correctly intraoperatively locate the spinal level on the patient from which corresponding fiducials had been selected in the volumetric image data. During this process, the surgeon needs to select the corresponding volumetric and intraoperative fiducial points, and also correctly correlate the intraoperatively selected fiducial points with the volumetric fiducial points on a one-to-one basis. This selection and correlation process is prone to human error, potentially leading to poor image registration and surgical errors.

SUMMARY

Systems and methods are provided for use in image-guided surgical procedures, in which intraoperatively acquired surface data is employed to verify the correspondence between intraoperatively selected fiducial points and volumetric fiducial points, where the volumetric fiducial points are selected based on volumetric image data. Segmented surface data obtained from the volumetric image data is registered to the intraoperative surface data using the intraoperative and volumetric fiducial points for initial surface alignment, and this process is repeated for other permutations of the correspondence between the intraoperatively fiducial points and the volumetric fiducial points. Quality measures may be determined that relate to the registration quality for each fiducial correspondence permutation, where the quality measures may be employed to assess of the likelihood that the initially prescribed fiducial correspondence is correct. A graphical representation may be generated for visually displaying the alignment of the registered surfaces for the different fiducial correspondence permutations.

Accordingly, in a first aspect, there is provided a method of performing intraoperative verification of fiducial correspondence, the method comprising:

obtaining volumetric image data pertaining to an anatomical region;

processing the volumetric image data to generate preliminary surface data characterizing an anatomical surface within the anatomical region;

obtaining input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

obtaining input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) employing the first preliminary registration to initiate and perform a first surface-based registration between the segmented surface data and the intraoperative surface data;

(iii) determining a first registration quality measure associated with a quality of the surface-based registration;

repeating steps (i) to (iii) for one or more permutations of the correspondence between the intraoperative fiducial points and the volumetric fiducial points, thereby performing one or more additional surface-based registrations and obtaining one or more additional registration quality measures respectively associated with the one or more additional surface-based registrations, wherein each additional registration quality measure is associated with a different permutation of the correspondence between the volumetric fiducial points and the intraoperative fiducial points; and providing feedback associated with the registration quality measures.

In another aspect, there is provided a method of performing intraoperative verification of fiducial correspondence, the method comprising:

obtaining volumetric image data pertaining to an anatomical region;

processing the volumetric image data to generate preliminary surface data characterizing an anatomical surface within the anatomical region;

obtaining input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

obtaining input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) determining a first registration quality measure associated with a quality of the preliminary registration;

repeating steps (i) and (ii) for one or more permutations of the correspondence between the intraoperative fiducial points and the volumetric fiducial points, thereby performing one or more additional preliminary registrations and obtaining one or more additional registration quality measures respectively associated with the one or more additional preliminary registrations, wherein each additional registration quality measure is associated with a different permutation of the correspondence between the volumetric fiducial points and the intraoperative fiducial points.

In another aspect, there is provided a method of performing intraoperative verification of fiducial correspondence, the method comprising:

obtaining volumetric image data pertaining to an anatomical region;

processing the volumetric image data to generate preliminary surface data characterizing an anatomical surface within the anatomical region;

obtaining input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

obtaining input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) employing the first preliminary registration to initiate and perform a first surface-based registration between the segmented surface data and the intraoperative surface data;

repeating steps (i) and (ii) for one or more permutations of the correspondence between the intraoperative fiducial points and the volumetric fiducial points, thereby performing one or more additional surface-based registrations, wherein each additional surface-based registrations is associated with a different permutation of the correspondence between the volumetric fiducial points and the intraoperative fiducial points; and generating a graphical representation of the first surface-based registration and the one or more additional surface-based registrations.

In another aspect, there is provided a system for performing intraoperative verification of fiducial correspondence, the system comprising a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

processing volumetric image data pertaining to an anatomical region to generate preliminary surface data characterizing an anatomical surface within the anatomical region;

receiving input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

receiving input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) employing the first preliminary registration to initiate and perform a first surface-based registration between the segmented surface data and the intraoperative surface data;

(iii) determining a first registration quality measure associated with a quality of the surface-based registration;

repeating steps (i) to (iii) for one or more permutations of the correspondence between the intraoperative fiducial points and the volumetric fiducial points, thereby performing one or more additional surface-based registrations and obtaining one or more additional registration quality measures respectively associated with the one or more additional surface-based registrations, wherein each additional registration quality measure is associated with a different permutation of the correspondence between the volumetric fiducial points and the intraoperative fiducial points; and providing feedback associated with the registration quality measures.

In another aspect, there is provided a system for performing intraoperative verification of fiducial correspondence, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

processing volumetric image data pertaining to an anatomical region to generate preliminary surface data characterizing an anatomical surface within the anatomical region;

receiving input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface; intraoperatively detecting, with a surface detection subsystem, intraoperative surface data characterizing an exposed surface region including at least a portion of the surface region of interest;

receiving input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) determining a first registration quality measure associated with a quality of the preliminary registration;

repeating steps (i) and (ii) for one or more permutations of the correspondence between the intraoperative fiducial points and the volumetric fiducial points, thereby performing one or more additional preliminary registrations and obtaining one or more additional registration quality measures respectively associated with the one or more additional preliminary registrations, wherein each additional registration quality measure is associated with a different permutation of the correspondence between the volumetric fiducial points and the intraoperative fiducial points.

In another aspect, there is provided a system for performing intraoperative verification of fiducial correspondence, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising: processing volumetric image data pertaining to an anatomical region to generate preliminary surface data characterizing an anatomical surface within the anatomical region;

receiving input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

receiving input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) employing the first preliminary registration to initiate and perform a first surface-based registration between the segmented surface data and the intraoperative surface data;

repeating steps (i) and (ii) for one or more permutations of the correspondence between the intraoperative fiducial points and the volumetric fiducial points, thereby performing one or more additional surface-based registrations, wherein each additional surface-based registrations is associated with a different permutation of the correspondence between the volumetric fiducial points and the intraoperative fiducial points; and generating a graphical representation of the first surface-based registration and the one or more additional surface-based registrations.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 2E shows the different possible permutations of the correspondence between the intraoperative fiducial points and the volumetric fiducial points.

FIGS. 3A-B show an example visualization of an intraoperative surface registered to segmented volumetric surface of the spine, where the fiducial correspondence is correct.

FIGS. 3C-D show an example visualization of an intraoperative surface registered to segmented volumetric surface of the spine, where the fiducial correspondence is incorrect.

FIGS. 4A-C illustrate different example methods of providing feedback based on the registration quality measures with or without graphical representations.

DETAILED DESCRIPTION

Figure 1:
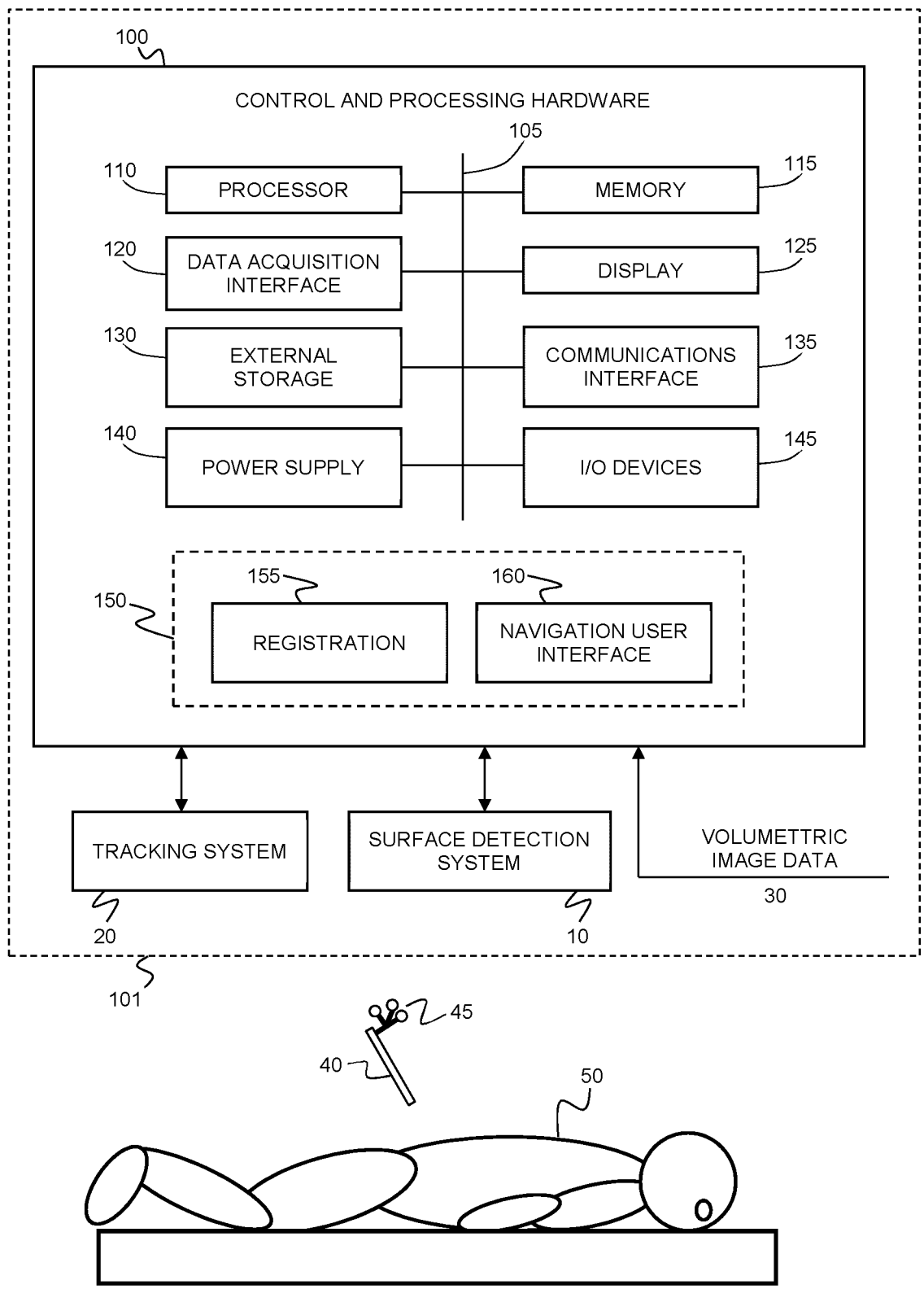
FIG. 1 shows an example system for performing intraoperative verification of fiducial selection and correspondence.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

When performing image-guided surgical navigation, volumetric image data, often obtained preoperatively, is intraoperatively displayed in a common frame of reference with the positions and orientations of intraoperatively tracked medical instruments. The intraoperative determination of the position and location of tracked medical instruments may be performed, for example, using an optical tracking system. However, in order to display the intraoperative positions and orientations of tracked medical instruments relative to the volumetric image data, the intraoperative position and orientation of the patient anatomy should also be determined.

The intraoperative determination of the position and orientation of the patient may be performed by identifying, in the frame of reference of the tracking system, the locations of intraoperative fiducial points that correspond to fiducial points that were pre-selected within the volumetric image data. Having established this relationship between the intraoperative frame of reference and the frame of reference of the volumetric image data based on corresponding fiducial points in each frame of reference, a transformation may be computed that transforms the volumetric image data into the intraoperative frame of reference, thereby facilitating intraoperative image-guided surgical navigation based on the volumetric image data. The transformation thus permits the display, on a user interface, of the positions and orientations of intraoperatively used surgical instruments in a common frame of reference with the volumetric image data. Intraoperative changes in the position and/or orientation of the patient may be tracked during navigation using a tracked reference frame attached to the patient.

The transformation between the volumetric frame of reference and the intraoperative frame of reference may be improved using the intraoperative detection of the topography of an exposed surface. For example, during the surgical procedure, an exposed surface of the patient may be dynamically tracked using a surface detection system, such as a structured light detection system. The intraoperative tracking of the exposed surface provides intraoperative surface data characterizing the topography of the exposed surface, and this intraoperative surface data may be employed to provide accurate registration between the volumetric frame of reference and the intraoperative frame of reference at one or more times during the surgical procedure.

Referring now to FIG. 1, an example system is shown for performing intraoperative registration using a surface detection system. The system includes a surface detection system 10 that is operably interfaced with control and processing hardware 100. The surface detection system 10 may be any suitable system for detecting, measuring, imaging, or otherwise determining the surface topography of one or more objects (such as, but not limited to, a region of an exposed spine of a patient 50) using optical radiation or sound waves (e.g. ultrasound). Non-limiting examples of suitable optical devices include laser range finders, photogrammetry systems, and structured light imaging systems, which project surface topography detection light onto a region of interest, and detect surface topography light that is scattered or reflected from the region of interest. The detected optical signals can be used to generate surface topography datasets consisting of point clouds or meshes. Other examples using sound waves for determining surface topography can include ultrasonography.

The example system may also include a tracking system 20, which may be employed to track the position and orientation of one or more medical instruments 40. The medical instrument 40 is shown having fiducial markers 45 attached thereto, and passive or active signals emitted from the fiducial markers 45 are detected by the tracking system 20 (e.g. a stereoscopic tracking system employing two tracking cameras). In an alternative example embodiment, the position and orientation of a medical instrument may be tracked via a surface detection subsystem 10, such as a structured light detection system, that is employed to detect the surface profile of a of at least a portion of the medical instrument, or structure attached thereto, and to determine the position and orientation of the medical instrument via comparison of the detected surface profile with a known surface profile.

Although not shown in FIG. 1, a tracked reference frame (e.g. a clamp with fiducial markers provided thereon or attached thereto) may be attached to the patient and may be tracked by the tracking system 20. Such a tracked reference frame may be employed for image-guided surgeries.

FIG. 1 also illustrates an example implementation of control and processing hardware 100, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 1 is illustrative of a non-limiting example embodiment, and is not intended to be limited to the components shown. Furthermore, one or more components of control and processing hardware 100 may be provided as an external component that is interfaced to a processing device. For example, as shown in the figure, one or both of the surface detection system 10 and the tracking system 20 may be included as a component of control and processing hardware 100 (as shown within the dashed line 101), or may be provided as one or more external devices.

Although only one of each component is illustrated in FIG. 1, any number of each component can be included in the control and processing hardware 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing hardware 100 may include many more or less components than those shown.

Control and processing hardware 100 may be implemented as one or more physical devices that are coupled to processor 110 through one of more communications channels or interfaces. For example, control and processing hardware 100 can be implemented using application specific integrated circuits (ASICs). Alternatively, control and processing hardware 100 can be implemented as a combination of hardware and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via hardware logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of hardware and/or software.

The control and processing hardware 100 is programmed with subroutines, applications or modules 150, which include executable instructions, which when executed by the one or more processors 110, causes the system to perform one or more methods described in the present disclosure. Such instructions may be stored, for example, in memory 115 and/or other internal storage. In particular, in the example embodiment shown, registration module 155 includes executable instructions for registering segmented surface data (obtained from the volumetric image data 30) with intraoperative surface data that is obtained using the surface detection system 10.

The registration module 155 may also be employed for computing registration quality measures associated with the quality of registration between the segmented surface data and the intraoperative surface data, thereby generating measures for verifying the correspondence between volumetric and intraoperative fiducial points, as explained in further detail below. The navigation user interface module 160 includes executable instructions for displaying a user interface for performing, for example, image-guided surgical procedures.

Figure 5A:
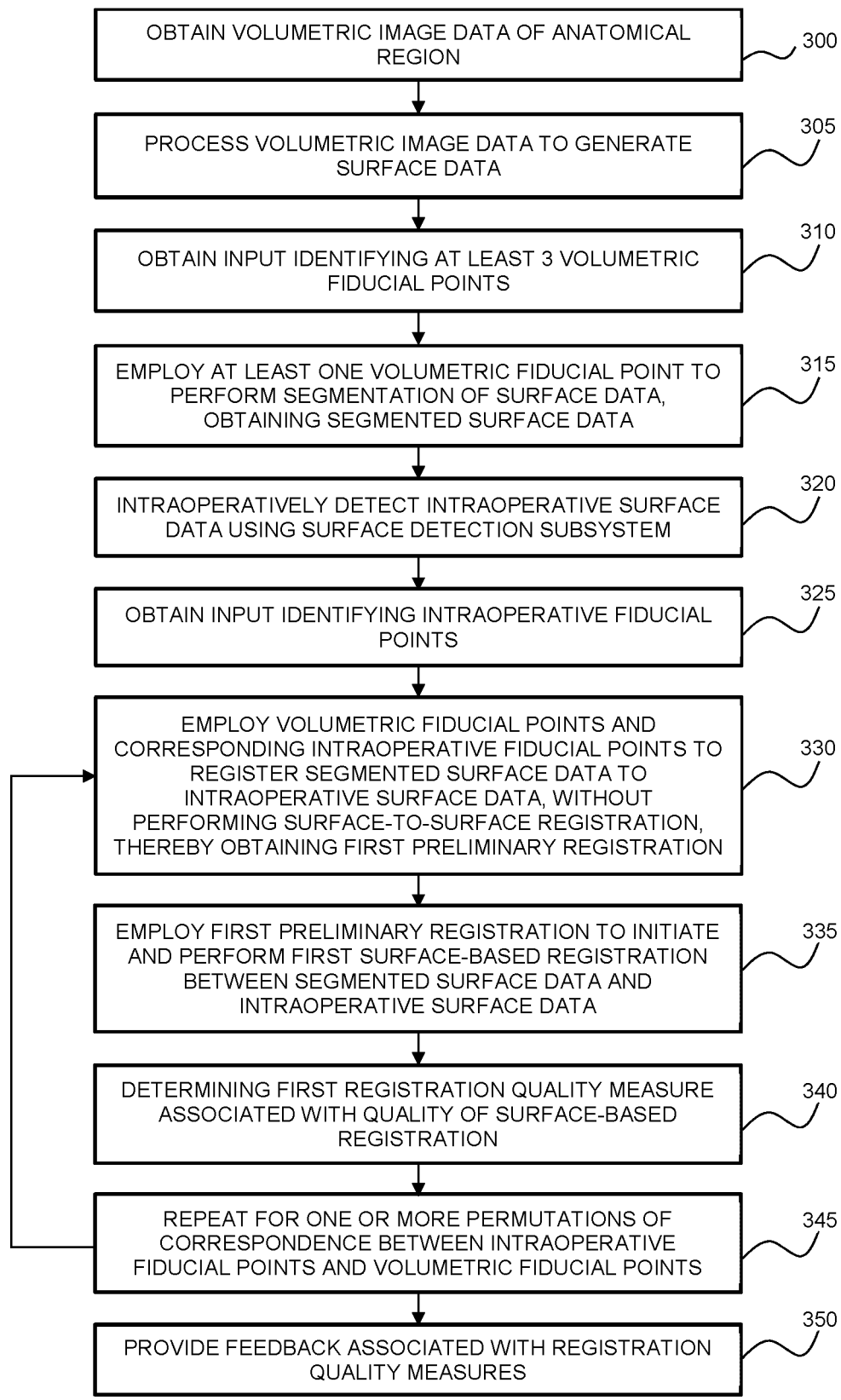
FIGS. 5A-B provide flow charts illustrating example methods of intraoperative verification of the correspondence between volumetric and intraoperative fiducial points.

Referring now to FIG. 5A, an example method is henceforth described for performing intraoperative registration of volumetric image data using a surface detection system, and performing verification of the correspondence of the intraoperative fiducial points and volumetric fiducial points. As described in detail below, in some example embodiments, the verification of fiducial correspondence may be achieved by performing registration between segmented surface data (obtained from volumetric image data) and intraoperative surface data, and comparing the quality of registration for different permutations of the correspondence between the volumetric and intraoperative fiducial points. In other example embodiments, visual inspection of the registered segmented surface data and intraoperative surface data can also be used, either alone, or to supplement the quality of registration, to provide the user with additional information to evaluate the different permutations of the correspondence of fiducial points.

It will be understood that some of the steps illustrated in the flow chart shown in FIG. 5A need not be performed in the order shown. In step 300, volumetric image data is obtained, preoperatively or intraoperatively. The volumetric image data may be obtained, for example, via imaging modalities such as, but not limited to, computed tomography (CT) and magnetic resonance imaging (MRI). Alternatively, the volumetric image data may be obtained intraoperatively, for example, using intraoperative CT or intraoperative MRI.

In order to perform registration between the intraoperative surface data and the volumetric image data, the volumetric image data is first processed to generate preliminary surface data associated with an anatomical region that is planned to be exposed during the medical procedure, as shown at step 305. The generation of the preliminary surface data permits surface-to-surface registration with the intraoperative surface data.

Figure 2A:
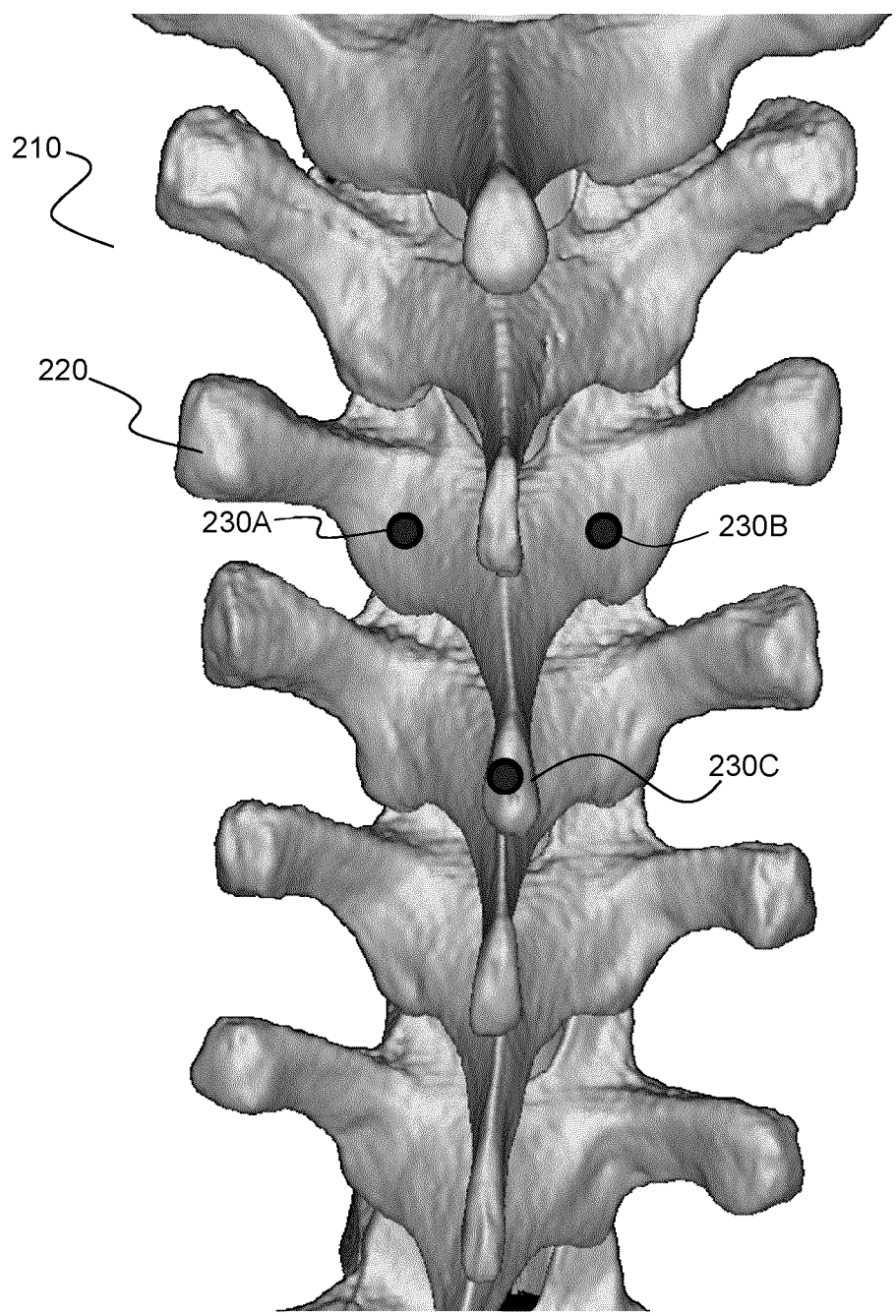
FIG. 2A illustrates an example multi-level surface generated by thresholding volumetric image data of the spine to determine a surface corresponding to bone, showing the pre-selected spinal level that is expected to correspond to a selected intraoperatively exposed spinal level. The figure also shows three volumetric fiducial points located at the pre-selected spinal level.

An example preliminary surface data generated from volumetric image data is shown in FIG. 2A for the example case of a spinal surgical procedure. As explained below, the forthcoming examples that pertain to spinal surgical procedures are not intended to be limiting, and it will be understood that the systems and methods described herein may be applied to a wide variety of surgical procedures (e.g. involving a wide variety of different anatomical regions and pathologies). In FIG. 2A, the preliminary surface data is generated as a multi-level image 210 of the spine. Many volumetric spinal levels can be seen, allowing the determination of the identity (i.e. level number) of a given volumetric spinal level. This multi-level surface 210, characterized by associated multi-level surface data, resides in the volumetric frame of reference that is associated with the volumetric image data.

The preliminary surface data may be generated according to a wide variety of methods. For example, a threshold (e.g. a bone threshold) may be selected and an isosurface may be generated from the volumetric image data using the marching cubes algorithm. Another example is to construct an isocontour from each 2D slice of a volumetric image data based on a suitable threshold, and stitching the slices together into a 3D surface.

The preliminary surface data may be employed for the selection of a set of at least three volumetric fiducial points, shown at 230A-C in FIG. 2A, and in step 310 of FIG. 5A. In the example case shown in FIG. 2A, the volumetric fiducial points 230A-C, which may be selected by an operator on a user interface displaying the multi-level surface data, identify a pre-selected spinal level 220 that is expected to be exposed during a surgical procedure.

The volumetric fiducial points (i.e. fiducial points in the volumetric frame of reference) are thus selected at or near a surface region of interest pertaining to the surgical procedure. One or more of these volumetric fiducial points may be employed to perform segmentation of the preliminary surface data, thereby obtaining segmented surface data characterizing the surface region of interest, as shown at step 315 of FIG. 5A. In the example case of a spinal surgical procedure illustrated in FIGS. 2A-C, the multi-level surface data may be processed based on one or more of the volumetric fiducial points 230A-C to generate the segmented surface data associated with the pre-selected level 220.

Figure 2B:
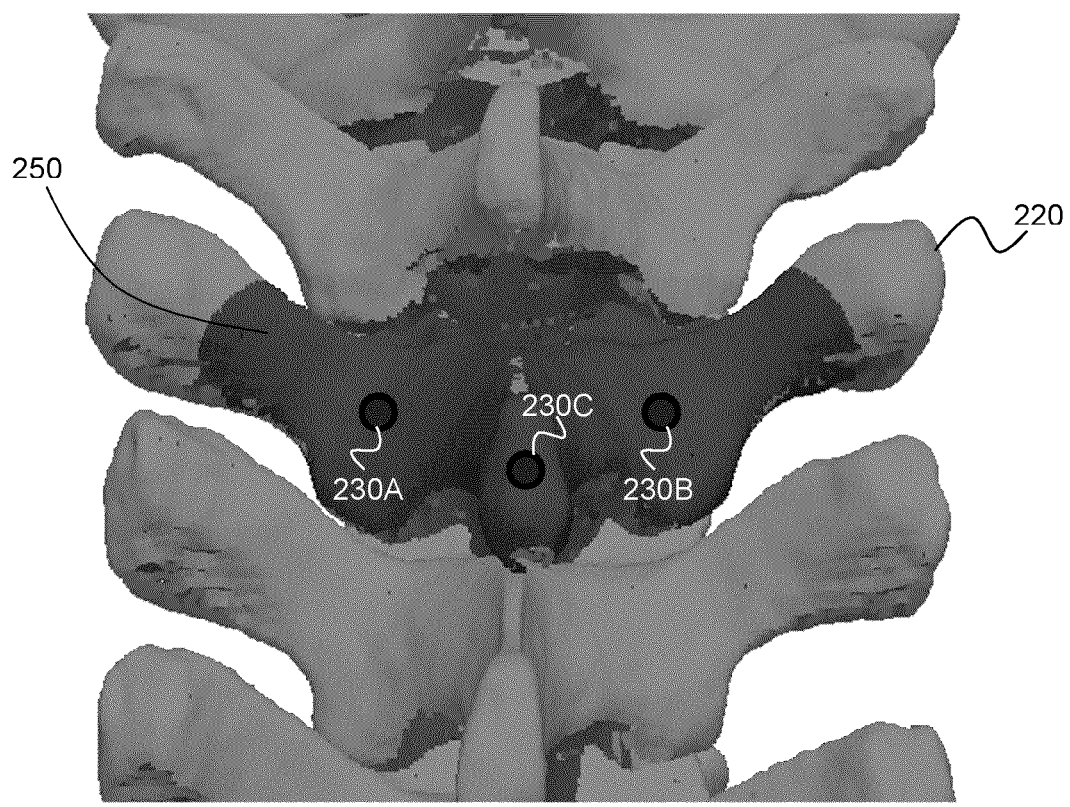
FIG. 2B illustrates an example segmented surface, obtained by segmenting the multi-level surface of FIG. 2A at the pre-selected spinal level (as identified by the volumetric fiducial points).

An example of the segmented surface data 250 is shown in FIG. 2B, which also shows the volumetric fiducial points 230A-C. The segmented surface data 250 includes surface data corresponding to the pre-selected spinal level 220.

Segmentation of the preliminary surface data to obtain the segmented surface data may be performed according to any suitable method. Non-limiting examples of surface segmentation methods include non-template-based methods and methods which utilize anatomical shape models. Non-template-based methods can utilize geometrical properties, such as connectivity, surface normals, and curvatures to determine the boundary of the segmented region, or statistical properties, such as variance from nearby neighboring points on the surface. Methods based on anatomical shape models can utilize a pre-computed atlas of vertebra as a template to perform the segmentation. Both classes of the methods can also be used in combination. In all these methods, one or more volumetric fiducial points can serve as a seed point to initialize the segmentation process. Alternatively, for segmentation methods which are fully automatic and operates on the entire volumetric data (which are usually based on anatomical atlases), one or more volumetric fiducials can be used to tag the level(s) of interest.

Having generated the segmented surface data corresponding to the surface region of interest in the volumetric frame of reference, the segmented surface data may be registered to the intraoperative surface data characterizing the exposed surface, detected using a surface detection system, as shown at step 320 of FIG. 5A. As noted above, the intraoperative surface data may be obtained using a surface detection system such as, but not limited to, a structured light detection system.

Figure 2C:
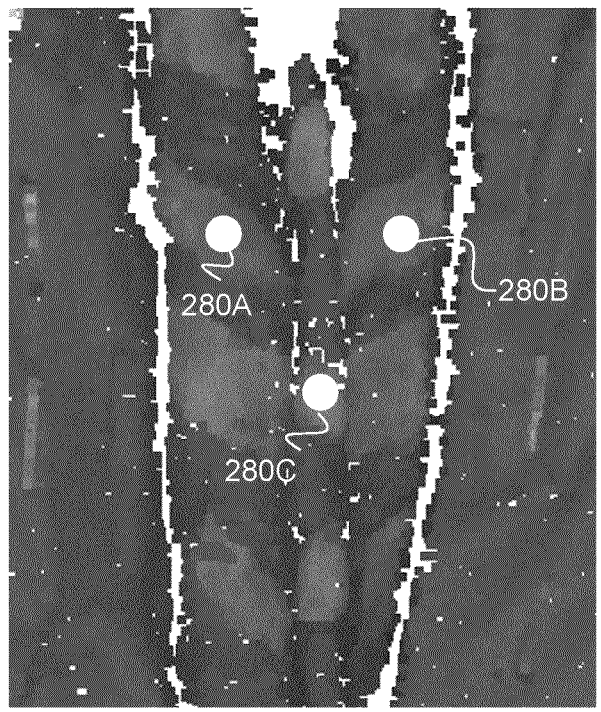
FIG. 2C illustrates an intraoperative surface detected using a surface detection system, showing several intraoperatively exposed spinal levels. Three intraoperative fiducial points, corresponding to the volumetric fiducial points, identify the intraoperatively selected spinal segment that is believed to correspond to the pre-selected spinal level in the volumetric frame of reference.
Figure 2D:
FIG. 2D provides a detailed view of the intraoperative surface shown in FIG. 2C.

FIG. 2C shows an example of intraoperative surface data detected using a structured light detection system. A zoomed in view is provided in FIG. 2D. In contrast to the multi-level surface data 210 shown in FIG. 2A, the intraoperative surface data only has partial bone exposed, and may contain multiple spinal levels in the field of view.

Prior to registering the segmented surface data to the intraoperative surface data, input is received that is indicative of the locations of intraoperative fiducial points. For example, FIG. 2C shows the identification of intraoperative fiducial points 280A-C in the intraoperative frame of reference, where each intraoperative fiducial point corresponds to a respective volumetric fiducial point, as shown at step 325 of FIG. 5A. The intraoperative fiducial points 280A-C thus identify, in the intraoperative frame of reference, the intraoperatively selected anatomical surface region (e.g. a selected spinal level) that is expected to correspond to (e.g. have the same spinal level as) the pre-selected selected surface region in the preliminary surface data that corresponds to the region associated with the volumetric fiducial points. The input can be received, for example, via the use of a tracked probe, such as the tracked probe 40 shown in FIG. 1, where the tracked probe is positioned with its tip at a desired intraoperative fiducial point, and input is provided by the user indicating that the location of the tracked probe corresponds to a given volumetric fiducial point.

It is also to be understood that the selection of intraoperative fiducial points and detection of intraoperative surface can be performed before the volumetric fiducial points are selected, that is, step 320 and 325 can be performed before 310 and 315, as long as they are performed before step 330, which utilize these data for performing the first preliminary registration.

Having generated the segmented surface data from the volumetric image data, registration may be performed between the intraoperative surface data and the segmented surface data, as shown at steps 330 and 335 of FIG. 5A.

Prior to performing surface-to-surface registration between the segmented surface data and the intraoperative surface data, the two surfaces may be initially aligned using a correspondence between the volumetric fiducial points and intraoperative fiducial points, where the intraoperative fiducial points are intraoperatively selected by an operator. Accordingly, as shown at step 330, the identified volumetric fiducial and respective intraoperative fiducial points may be employed to perform an initial registration (based on the correspondence of the volumetric and intraoperative fiducial points).

As shown at step 335, a suitable surface-to-surface registration method (algorithm) may then be employed to perform registration between the segmented surface data and the intraoperative surface data. It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

The preceding example method of performing registration is effective when the intraoperative fiducial points are selected such that: (i) the locations of the intraoperative fiducial points, relative to the patient anatomy, are in suitable alignment with locations of the volumetric fiducial points, relative to the patient anatomy, in the volumetric frame of reference. For example, with reference to FIGS. 2B and 2C, it can be clearly seen that the locations of the three intraoperative fiducial points 280A-C, relative to the anatomical features of the selected spinal level 220, are spatially aligned with the locations of the volumetric fiducial points 230A-C.

However, this spatial alignment between volumetric fiducial points and intraoperative fiducial points is insufficient to ensure correct and suitably accurate registration between the segmented surface data and the intraoperative surface data. Indeed, in order to ensure correct registration, correspondence between the identity of the volumetric fiducial points and the intraoperative fiducial points should also be correctly prescribed.

For example, as shown in FIG. 2E, it can be seen that there are six different possible permutations of the correspondence between the identity of the intraoperative fiducial points and the identity of the volumetric fiducial points. Permutation (i) provides a correct correspondence between the intraoperative fiducial points and the volumetric fiducial points, where volumetric fiducial point A maps to intraoperative fiducial point A, volumetric fiducial point B maps to intraoperative fiducial point B, and volumetric fiducial point C maps to intraoperative fiducial point C. However, permutations (ii) to (vi) result in incorrect prescriptions between the respective fiducial points.

In various example embodiments of the present disclosure, verification of the prescribed fiducial correspondence may be performed by performing registration between the intraoperative surface data and the segmented surface data for one or more permutations of the fiducial correspondence, and providing feedback to an operator that facilitates an assessment as to whether or not the initially prescribed fiducial correspondence is likely to be correct. In some example implementations, all possible fiducial correspondence perturbations may be assessed via registration. The feedback provided to the operator may facilitate the identification of a different fiducial correspondence that provides improved registration relative to the initially prescribed fiducial correspondence.

In one example embodiment, the feedback provided to an operator may include, and/or be based on, registration quality measures that are computed for each fiducial correspondence permutation. For example, as shown in steps 340 of FIG. 5A, a registration quality measure may be determined for the initially prescribed fiducial correspondence, and steps 330-340 may be repeated for one or more alternative fiducial correspondence permutations (e.g. one or more of permutations (ii) to (vi) shown in FIG. 2E), thereby providing, for each different fiducial correspondence permutation, one or more registration quality measures that characterize the quality of the respective registration.

In one example implementation, the determination of additional surface-based registrations and additional registration quality measures for other fiducial correspondence permutations are only performed when the first registration quality measure is less than a pre-selected threshold. For example, when the registration quality measure pertaining to the prescribed fiducial correspondence fails to exceed the pre-selected threshold, the additional surface-based registrations and the additional registration quality measures pertaining to additional fiducial correspondence permutations may be generated until a given additional registration quality measure exceeds the pre-threshold, or until all permutations of fiducial correspondences between the volumetric fiducial points and the intraoperative fiducial points have been assessed.

One example measure of registration quality can be the registration error, which describes the mean distance between points of the segmented surface data to the registered intraoperative surface data. Another example measure of registration quality is the standard deviation of the distances between points of the segmented surface data to the registered intraoperative surface data. An additional example measure of registration quality is the number of points that are matched between the surface data. Yet another example is how the points from the intraoperative surface data are spatially distributed on the segmented surface data after registration, such as the ratio of the number of points to the surface area of the segmented surface data. These metrics, or other suitable registration quality measures, can be used alone or in combination. One example method to combine these metrics is to evaluate the ratio of the different metrics. If two metrics disagree, the choice for a more desired registration quality can be based on the one metric whose relative difference is greatest. Another example to combine the use of different metrics is to train a computational model by presenting it with examples of registrations at correct and incorrect spinal levels. Examples of such models can include a logistic regression classifier, a random forest, a support vector machine, or a neural network, which can be used to calculate a registration quality measure.

Another method to evaluate the registration quality is to enable an operator to visually inspect the intraoperative surface 410 registered to the segmented surface data 420 in the volumetric frame of reference, as shown in FIGS. 3A-D. FIGS. 3A-B show graphical visualizations of the registered surfaces based on the fiducial correspondence permutation (i) shown in FIG. 2E. Two views of the same data are shown, portrayed by FIG. 3A and FIG. 3B. FIGS. 3C and 3D show graphical visualizations of the registered surfaces based on the fiducial correspondence shown in permutation (vi) shown in FIG. 2E.

Visually, for a registration that is appropriate for navigation, of which the correct correspondence between the fiducials was selected, the two surfaces are overlaid where there exist regions 430 with significant overlap between the two surfaces. Alternatively, if the fiducial correspondence is incorrect, the registered intraoperative surface and segmented surface data looks mismatched anatomically, with less regions of overlap.

The user, when presented with the visualizations shown in FIGS. 3A-D, may visually assess the quality of the registrations for the different permutations and determine that the permutation shown in FIGS. 3A-B is correct and that the permutation shown in FIGS. 3C-D is incorrect. The visualizations shown in FIGS. 3A-D permit the operator to determine that the fiducial correspondence of FIGS. 3C-D pertains to an erroneous selection in which the fiducial on the left lamina is switched with the fiducial on the right lamina.

Although the example implementation shown in FIGS. 3A-D show two views of the registered surfaces per permutation, it will be understood that any number of views may be provided. For example, in one example implementation, one or more views may be provided that are rotatable, permitting the operator to assess the registration from multiple perspectives. The rotation of a given view may be automated, permitting the operator to assess the registration from multiple perspectives without having to interact with the user interface. In addition, the transparency of the registered surfaces may be adjusted, for example, at 50% transparency, which may permit internal structures to be visualized.

In one example embodiment, the graphical visualization may be configured to provide a visual indication of regions of high spatial overlap. For example, regions having a local point cloud separation that is less than a pre-selected threshold (e.g. regions 430 of FIGS. 3A and 3B) may be shown with a different format that is discernable by an observer. For example, regions of such high overlap may be shown with a different colour, point size, point shape, intensity, thickness, or texture.

Visual inspection of the registration between segmented surface and intraoperative surface may be used alone, or in combination with registration quality measures, to enable the surgeon to better infer whether or not the prescribed fiducial correspondence is likely to be correct.

As noted above, the registration quality measures may be employed to provide feedback for evaluating and verifying the validity of prescribed fiducial correspondence measures. Therefore, in some example embodiments, feedback associated with the registration quality measures may be provided, where the feedback is suitable for inferring whether or not the prescribed fiducial correspondence is likely to be correct. This feedback can take a wide variety of different forms, such as providing the registration quality measures, or one or more other measures derived from the registration quality measures. For example, in the case that the registration quality measure associated initially prescribed fiducial correspondence is not the highest registration quality measure, the feedback may indicate that the intraoperatively selected spinal level may not correspond to the pre-selected spinal level. In one example implementation, the feedback can include a display of the registration quality measures for the registrations associated with the different fiducial correspondence permutations. For example, as shown in FIG. 4A, the feedback can be text-based, wherein the user is notified that the intraoperative fiducials may not correctly correspond to the volumetric fiducial points, and a suggestion and option is made available to re-do registration and/or select a different fiducial correspondence.

Figure 4B:
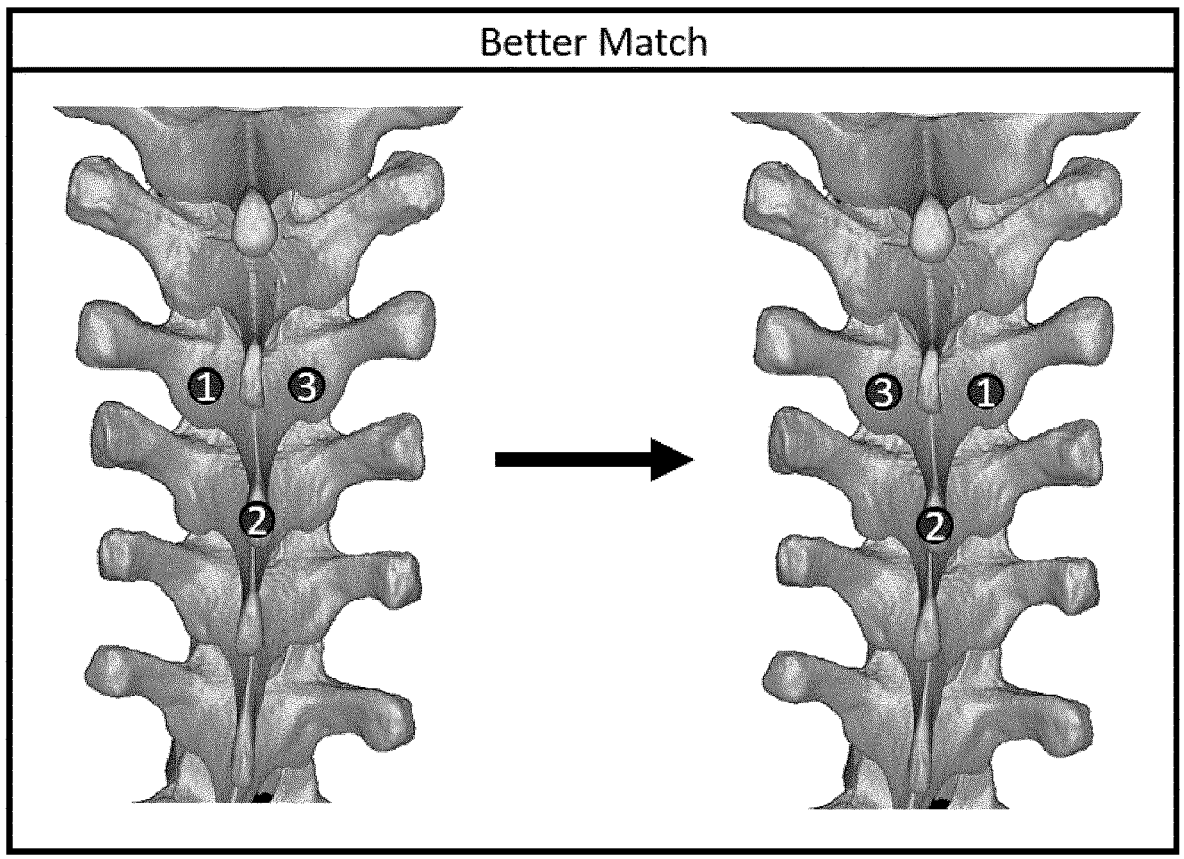
Figure 4C:
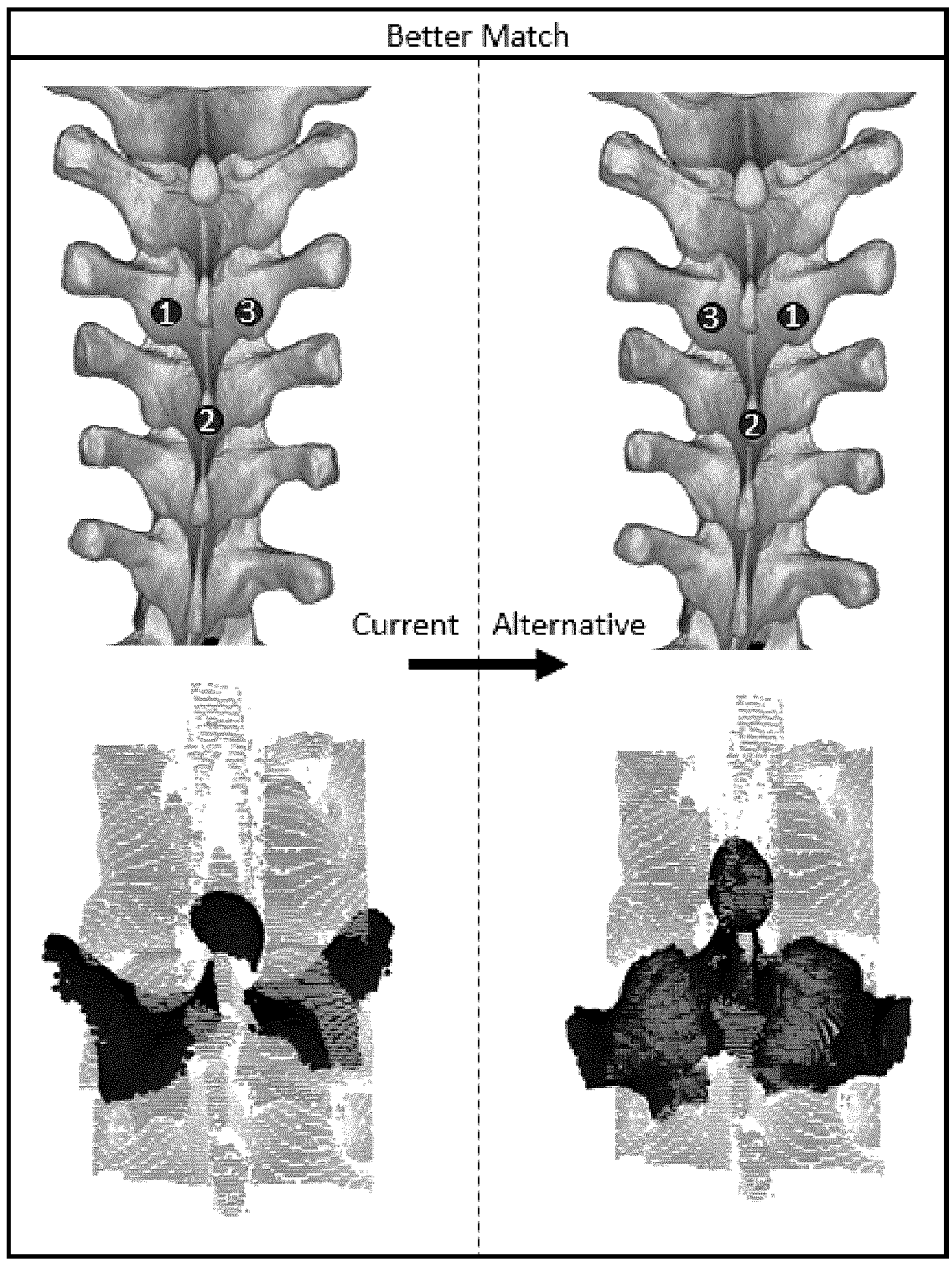

Alternatively, a more graphical presentation may be used. As shown in FIG. 4B, a single suggestion is provided to the user to indicate which fiducial correspondence permutation resulted in the highest registration quality. Furthermore, visualization of the alignment of the intraoperative surface data with the segmented surface data (e.g. as shown in FIGS. 3A-D) may be used to support a suggestion, where a registered intraoperative surface data with the segmented surface in the volumetric frame of reference is shown, providing a visualization of the registration quality that would be obtained if an alternative fiducial correspondence is selected. An example of this type of feedback is shown in FIG. 4C.

In one example implementation, the feedback can include estimates of the probability of the initial fiducial correspondence permutation being correct, based on the registration quality measures. One such probability estimate can be derived based on the distribution of distances between points of the segmented surface data to the registered intraoperative surface data. The distributions corresponding to the different registrations can be compared by any suitable statistical tests. If the distributions can be approximated by a normal distribution, a Z-test may be used. Alternatively, nonparametric tests such as the Kolmogorov-Smirnov test can be employed.

In some example implementations, the feedback provided to the operator need not include quality measures pertaining to the quality of the different registrations. For example, as shown in FIGS. 3A-D, the quality of the registrations associated with the different fiducial correspondence permutations may be assessed based on a graphical representation of the alignment between the respective surfaces.

Figure 5B:
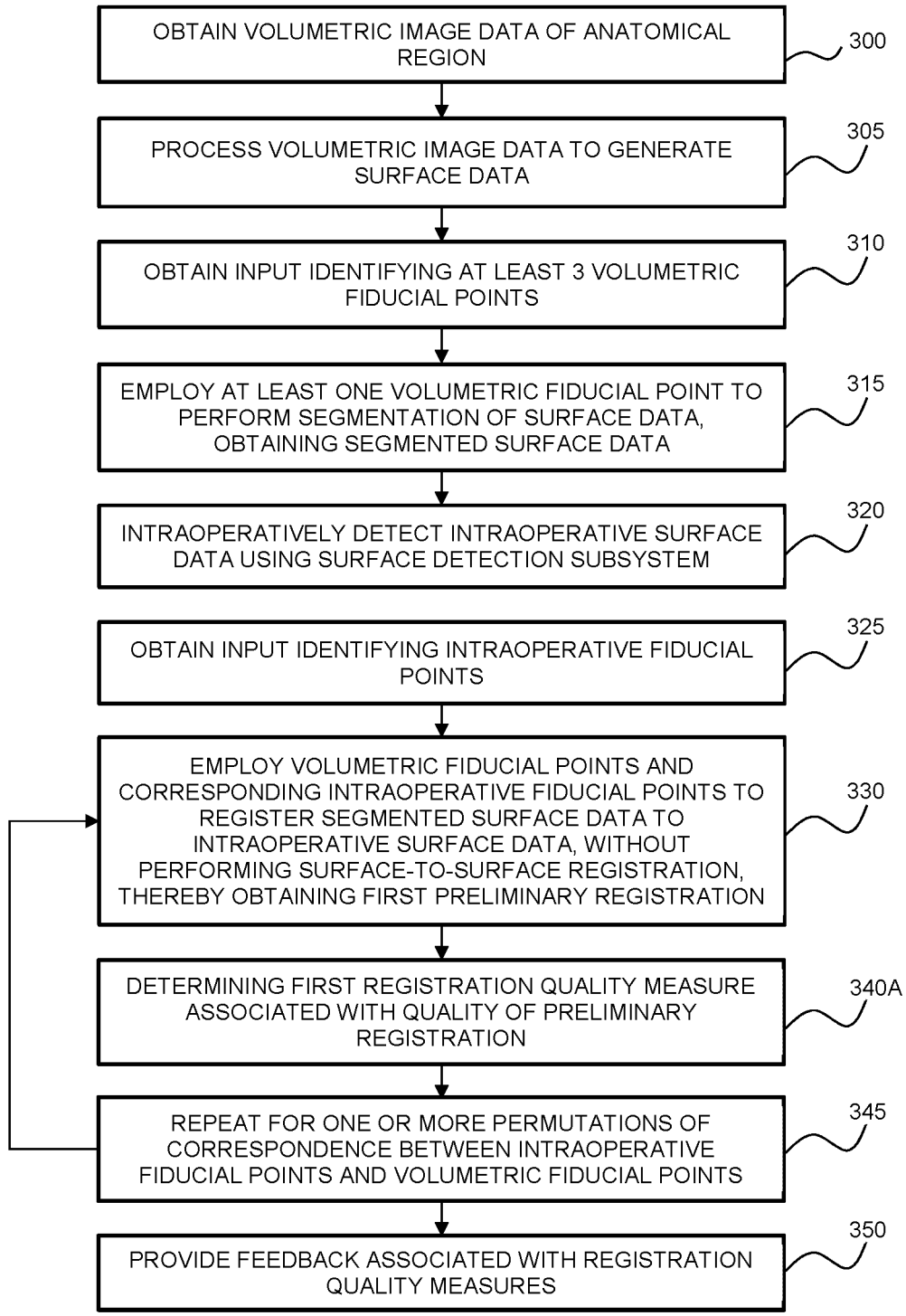

Although the example embodiment shown in FIG. 5A includes the step of performing surface-to-surface registration between the segmented surface data and the intraoperative surface data, it will be understood that in other example implementations, this step need not be performed in order to verify the selected correspondence between the volumetric fiducial points and the intraoperative fiducial points. For example, as shown in the flow chart provided in FIG. 5B, the registration quality measures may be determined based on the preliminary registration, in the absence of surface-to-surface registration.

The example methods disclosed herein may be beneficial for surgical procedures involving anatomical regions with high degrees of symmetry (e.g. about an axis or plane). In such cases, for example, checking only for the fiducial registration error may not enable the detection of mismatched fiducials selected from the image and from the patient. In some cases, mismatched fiducials (incorrect fiducial correspondence) can occur when anatomies are misidentified. Such mismatch can also occur when there is miscommunication between the operator of a navigation system, who may be assisting a surgeon by calling out the fiducial that the surgeon is supposed to pick next. Finally, mismatched fiducials can occur when the instructions are not clear from the graphical user interface that is instructing the surgeon which fiducial to select next, or the instructions are misinterpreted by the surgeon.

An example anatomical region for which checking for the fiducial registration error may not be sufficient is the spine, which is highly symmetric about the sagittal plane. Fiducials may be selected one on the left lamina, one of the right lamina, and one on the spinous process. The initial fiducial registration error may appear to be of good quality even if the ordering of the left and right lamina fiducials is reversed. However, this can lead to a registration that is not acceptable for navigation. Another example is for cranial and maxillofacial surgeries, where the skull is highly symmetric about the sagittal plane. Fiducials may be selected on the left and right supraorbital ridge and one on the glabella, where reversal of the left and right fiducials may not be detectable by fiducial registration error alone.

It is to be understood that although the examples described above do not involve attachment of physical fiducials, such as magnetic resonance and/or radio-opaque markers, to assist in the registration process (which is sometimes used in cranial and maxillofacial surgeries), the present disclosure is applicable for such procedures as well. Incorrect fiducial correspondence is still possible with physical fiducials, and registration quality measures can be generated using the methods described above. Furthermore, graphical visualizations of the registered data can additionally or alternatively be provided, as described above.

In one embodiment, the registration between the segmented surface data and the intraoperative surface data may be achieved without segmentation (or cropping) of the intraoperative surface data, even though the intraoperative surface data may include surface topography extending beyond the surface region of interest. For example, in the case of spinal surgery involving a selected spinal level, the additional surface topography may include regions such as adjacent spinal levels. In one example implementation, these regions may be retained because the segmented surface data contains only regions belonging to the surface region of interest due to its segmentation. For example, in the case of a spinal procedure, provided that the segmented surface data is initially spatially aligned to an intraoperatively selected spinal level, and only spatially extends within the spatial region corresponding to this level, the presence of additional spinal levels will not affect the registration quality.

However, it will be understood that in some example embodiments, the intraoperative surface data may be segmented to a spatial region pertaining to the surface region of interest, prior to performing registration. In one example implementation, this segmentation may be achieved, for example, based on an expected spatial extend relative to one or more of the intraoperative fiducial points. The expected spatial extent may be determined, for example, based on atlas data, or, for example, based on the spatial extent of the segmented surface data corresponding to the surface region of interest in the volumetric frame of reference.

Although some of the preceding example embodiments pertain to spinal surgical procedures involving a selected intraoperative spinal level based on registration between segmented surface data (obtained from volumetric image data) and intraoperative surface data, it will be understood that these embodiments may be readily adapted to involve verification, and registration, using multiple contiguous levels. For example, the verification methods disclosed above may employ, instead of a single level, two or more contiguous spinal levels (i.e. spinal levels that are in sequence; e.g. levels 2 and 3, or levels 4, 5 and 6). For example, in the aforementioned example verification embodiment involving the registration of segmented surface data with the intraoperative surface data and adjacent segmented surface data with the intraoperative surface data, the segmented surface data may correspond to two or more contiguous spinal levels. In such a case, the three or more volumetric fiducial points may span the set of contiguous spinal levels of the segmented surface data, and the intraoperative fiducial points may span the set of contiguous spinal levels of the intraoperative surface data.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing intraoperative verification of fiducial correspondence, the method comprising:

obtaining volumetric image data pertaining to an anatomical region;

processing the volumetric image data to generate preliminary surface data characterizing an anatomical surface within the anatomical region;

obtaining input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

obtaining input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) employing the first preliminary registration to initiate and perform a first surface-based registration between the segmented surface data and the intraoperative surface data;

(iii) determining a first registration quality measure associated with a quality of the surface-based registration;

repeating steps (i) to (iii) for one or more permutations of the correspondence between the intraoperative fiducial points and the volumetric fiducial points, thereby performing one or more additional surface-based registrations and obtaining one or more additional registration quality measures respectively associated with the one or more additional surface-based registrations, wherein each additional registration quality measure is associated with a different permutation of the correspondence between the volumetric fiducial points and the intraoperative fiducial points; and providing feedback associated with the registration quality measures.

2. The method according to claim 1 wherein the preliminary surface data characterizes one or more bone surfaces.

3. The method according to claim 2 wherein the preliminary surface data characterizes bone surfaces corresponding to one or more spinal levels.

4. The method according to claim 3 wherein the surface region of interest comprises one or more spinal levels.

5. The method according to claim 1 wherein the preliminary surface data characterizes a soft tissue surface.

6. The method according to claim 1 wherein the feedback is indicative of the fiducial correspondence having a highest associated registration quality measure.

7. The method according to claim 1 wherein the feedback is indicative of whether or not the first registration quality measure is the registration quality measure associated with a highest registration quality.

8. The method according to claim 1 wherein when the first registration quality measure fails to exceed a threshold, the additional surface-based registrations and the additional registration quality measures are generated until a given additional registration quality measure exceeds the threshold, or until all permutations of fiducial correspondences between the volumetric fiducial points and the intraoperative fiducial points have been assessed.

9. The method according to claim 1 wherein the one or more additional surface-based registrations and the determination of the one or more additional registration quality measures are only performed when the first registration quality measure is less than a threshold.

10. The method according to claim 1 further comprising generating a graphical representation of the first surface-based registration and the one or more additional surface-based registrations.

11. A method of performing intraoperative verification of fiducial correspondence, the method comprising:
  obtaining volumetric image data pertaining to an anatomical region;
  processing the volumetric image data to generate preliminary surface data characterizing an anatomical surface within the anatomical region;
  obtaining input identifying at least three volumetric fiducial points associated with the preliminary surface data;
  employing at least one of the volumetric fiducial points to perform segmentation on the preliminary surface data, thereby obtaining segmented surface data characterizing a surface region of interest within the anatomical surface;
  intraoperatively detecting, with a surface detection subsystem, intraoperative surface data characterizing an exposed surface region including at least a portion of the surface region of interest;
  obtaining input identifying at least three intraoperative fiducial points associated with the intraoperative surface data, each intraoperative fiducial point corresponding to a respective volumetric fiducial point, according to a prescribed fiducial correspondence;
  (i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;
  (ii) determining a first registration quality measure associated with a quality of the preliminary registration;
  repeating steps (i) and (ii) for one or more permutations of the correspondence between the intraoperative fiducial points and the volumetric fiducial points, thereby performing one or more additional preliminary registrations and obtaining one or more additional registration quality measures respectively associated with the one or more additional preliminary registrations, wherein each additional registration quality measure is associated with a different permutation of the correspondence between the volumetric fiducial points and the intraoperative fiducial points.

12. The method according to claim 11 wherein the preliminary surface data characterizes one or more bone surfaces.

13. The method according to claim 12 wherein the preliminary surface data characterizes bone surfaces corresponding to one or more spinal levels.

14. The method according to claim 13 wherein the surface region of interest comprises one or more spinal levels.

15. The method according to claim 11 wherein the preliminary surface data characterizes a soft tissue surface.

16. The method according to claim 11 further comprising providing feedback associated with the registration quality measures.

17. The method according to claim 11 wherein the registration quality measures are initial registration quality measures, the method further comprising, for each fiducial correspondence permutation having an associated registration measure that satisfies a pre-selected criterion:
  employing an associated preliminary registration to initiate and perform a surface-based registration between the segmented surface data and the intraoperative surface data; and
  determining a secondary registration quality measure associated with a quality of the surface-based registration; and
  providing feedback associated with the secondary registration quality measures.

18. The method according to claim 17 wherein an order of performing the surface-based registrations for the fiducial correspondence permutations having associated registration quality measures that satisfy the pre-selected criterion is determined based on the magnitude of the associated initial registration quality measures.

19. A method of performing intraoperative verification of fiducial correspondence, the method comprising:
  obtaining volumetric image data pertaining to an anatomical region;
  processing the volumetric image data to generate preliminary surface data characterizing an anatomical surface within the anatomical region;
  obtaining input identifying at least three volumetric fiducial points associated with the preliminary surface data;
  employing at least one of the volumetric fiducial points to perform segmentation on the preliminary surface data, thereby obtaining segmented surface data characterizing a surface region of interest within the anatomical surface;
  intraoperatively detecting, with a surface detection subsystem, intraoperative surface data characterizing an exposed surface region including at least a portion of the surface region of interest;
  obtaining input identifying at least three intraoperative fiducial points associated with the intraoperative surface data, each intraoperative fiducial point corresponding to a respective volumetric fiducial point, according to a prescribed fiducial correspondence;
  (i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;
  (ii) employing the first preliminary registration to initiate and perform a first surface-based registration between the segmented surface data and the intraoperative surface data;
  repeating steps (i) and (ii) for one or more permutations of the correspondence between the intraoperative fiducial points and the volumetric fiducial points, thereby performing one or more additional surface-based registrations, wherein each additional surface-based registrations is associated with a different permutation of the correspondence between the volumetric fiducial points and the intraoperative fiducial points; and generating a graphical representation of the first surface-based registration and the one or more additional surface-based registrations.

20. The method according to claim 19 wherein the preliminary surface data characterizes one or more bone surfaces.

21. The method according to claim 20 wherein the preliminary surface data characterizes bone surfaces corresponding to one or more spinal levels.

22. The method according to claim 21 wherein the surface region of interest comprises one or more spinal levels.

23. The method according to claim 19 wherein the preliminary surface data characterizes a soft tissue surface.

24. A system for performing intraoperative verification of fiducial correspondence, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing volumetric image data pertaining to an anatomical region to generate preliminary surface data characterizing an anatomical surface within the anatomical region;
receiving input identifying at least three volumetric fiducial points associated with the preliminary surface data;
employing at least one of the volumetric fiducial points to perform segmentation on the preliminary surface data, thereby obtaining segmented surface data characterizing a surface region of interest within the anatomical surface;
intraoperatively detecting, with a surface detection subsystem, intraoperative surface data characterizing an exposed surface region including at least a portion of the surface region of interest;
receiving input identifying at least three intraoperative fiducial points associated with the intraoperative surface data, each intraoperative fiducial point corresponding to a respective volumetric fiducial point, according to a prescribed fiducial correspondence;
(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;
(ii) employing the first preliminary registration to initiate and perform a first surface-based registration between the segmented surface data and the intraoperative surface data;
(iii) determining a first registration quality measure associated with a quality of the surface-based registration;
repeating steps (i) to (iii) for one or more permutations of the correspondence between the intraoperative fiducial points and the volumetric fiducial points, thereby performing one or more additional surface-based registrations and obtaining one or more additional registration quality measures respectively associated with the one or more additional surface-based registrations, wherein each additional registration quality measure is associated with a different permutation of the correspondence between the volumetric fiducial points and the intraoperative fiducial points; and providing feedback associated with the registration quality measures.

25. A system for performing intraoperative verification of fiducial correspondence, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing volumetric image data pertaining to an anatomical region to generate preliminary surface data characterizing an anatomical surface within the anatomical region;
receiving input identifying at least three volumetric fiducial points associated with the preliminary surface data;
employing at least one of the volumetric fiducial points to perform segmentation on the preliminary surface data, thereby obtaining segmented surface data characterizing a surface region of interest within the anatomical surface;
intraoperatively detecting, with a surface detection subsystem, intraoperative surface data characterizing an exposed surface region including at least a portion of the surface region of interest;
receiving input identifying at least three intraoperative fiducial points associated with the intraoperative surface data, each intraoperative fiducial point corresponding to a respective volumetric fiducial point, according to a prescribed fiducial correspondence;
(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;
(ii) determining a first registration quality measure associated with a quality of the preliminary registration;
repeating steps (i) and (ii) for one or more permutations of the correspondence between the intraoperative fiducial points and the volumetric fiducial points, thereby performing one or more additional preliminary registrations and obtaining one or more additional registration quality measures respectively associated with the one or more additional preliminary registrations, wherein each additional registration quality measure is associated with a different permutation of the correspondence between the volumetric fiducial points and the intraoperative fiducial points.

26. A system for performing intraoperative verification of fiducial correspondence, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing volumetric image data pertaining to an anatomical region to generate preliminary surface data characterizing an anatomical surface within the anatomical region;

receiving input identifying at least three volumetric fiducial points associated with the preliminary surface data;

employing at least one of the volumetric fiducial points to perform segmentation on the preliminary surface data, thereby obtaining segmented surface data characterizing a surface region of interest within the anatomical surface;

intraoperatively detecting, with a surface detection subsystem, intraoperative surface data characterizing an exposed surface region including at least a portion of the surface region of interest;

receiving input identifying at least three intraoperative fiducial points associated with the intraoperative surface data, each intraoperative fiducial point corresponding to a respective volumetric fiducial point, according to a prescribed fiducial correspondence;

(i) employing the volumetric fiducial points and the corresponding intraoperative fiducial points to register the segmented surface data to the intraoperative surface data, without performing surface-to-surface registration, thereby obtaining a first preliminary registration based on prescribed fiducial correspondence between the volumetric fiducial points and the intraoperative fiducial points;

(ii) employing the first preliminary registration to initiate and perform a first surface-based registration between the segmented surface data and the intraoperative surface data;

repeating steps (i) and (ii) for one or more permutations of the correspondence between the intraoperative fiducial points and the volumetric fiducial points, thereby performing one or more additional surface-based registrations, wherein each additional surface-based registrations is associated with a different permutation of the correspondence between the volumetric fiducial points and the intraoperative fiducial points; and generating a graphical representation of the first surface-based registration and the one or more additional surface-based registrations.

* * * * *